US005460958A

United States Patent [19]

Nakano et al.

[11] Patent Number: 5,460,958

[45] Date of Patent: Oct. 24, 1995

[54] **PROCESS FOR PRODUCING L-ISOLEUCINE BY S-2-AMINOETHYL-L-CYSTEINE OR D-SERINE RESISTANT STRAINS OF *E COLI***

[75] Inventors: Tetsuo Nakano, Machida; Tomoki Azuma, Chiba; Yoshiyuki Kuratsu, Hofu, all of Japan

[73] Assignee: Kyowa Hakko Kogyo Co., Ltd., Tokyo, Japan

[21] Appl. No.: 141,078

[22] Filed: Oct. 26, 1993

[51] Int. Cl.$^{6}$ .................................................... C12P 13/06

[52] U.S. Cl. ........................ 435/116; 435/252.8; 435/849

[58] Field of Search ................................ 435/116, 252.8, 435/849

[56] References Cited

FOREIGN PATENT DOCUMENTS 0130071 6/1984 European Pat. Off. .

OTHER PUBLICATIONS

Herrmann et al, (Ed.), *Amino Acids: Biosynthesis and Genetic Regulation,* Addison–Wesley Publishing Co.: London, 1983, pp. 415–416.

Inuzuka et al., "Fermentative Production of L–isoleucine", *Chemical Abstracts* vol. 87, No. 132324 1977.

Chemical Abstracts, vol. 89, No. 17, Oct. 23, 1978 No. 145017h.

Chemical Abstracts, vol. 83, No. 23, Dec. 8, 1975 No. 191345.

*Primary Examiner*—Marian C. Knode
*Assistant Examiner*—Maria L. Osoteo
*Attorney, Agent, or Firm*—Antonelli, Terry, Stout & Kraus

[57] ABSTRACT

A process for the production of L-isoleucine using the microorganism, *Escherichia coli* H-8670 (FERM BP-4051) which has resistance to 0.2 g/l S-(2-aminoethyl)-L-cysteine or *Escherichia coli* H-8683 (FERM BP-4052) which has a resistance of 20 g/l of D-serine. The microorganism is cultured in a nutrient medium for a time and under conditions sufficient to produce L-isoleucine and the L-isoleucine is recovered from the medium.

4 Claims, No Drawings

PROCESS FOR PRODUCING L-ISOLEUCINE BY S-2-AMINOETHYL-L-CYSTEINE OR D-SERINE RESISTANT STRAINS OF *E COLI*

RELATED APPLICATION

The present invention is related generally to the invention disclosed in U.S. application Ser. No. 973452 filed on Nov. 9, 1992 (EP-A-0542487), now U.S. Pat. No. 5,362,637 and entitled "Process for Producing L-Isoleucine".

BACKGROUND OF THE INVENTION

The present invention relates to a process for producing L-isoleucine by culturing a microorganism belonging to the genus Escherichia and having resistance to S-(2-aminoethyl)-L-cysteine or D-serine and an ability to produce L-isoleucine. L-Isoleucine is an amino acid which is useful as a medicament, a food additive and an additive for animal feed.

With respect to the direct fermentation process for production of L-isoleucine, various processes have been known; for example, a process by the use of a microorganism belonging to the genus Brevibacterium or Corynebacterium and having resistance to α-amino-β-hydroxyvaleric acid, with additionally imparted resistance to one or more agents selected from ethionine, β-(2-thiazolyl)-DL-alanine and S-(2-aminoethyl)-L-cysteine (Japanese Published Unexamined Patent Application No. 101582/75); and a process by the use of a microorganism belonging to the genus Corynebacterium and having resistance to S-(2-aminoethyl)-L-cysteine (Japanese Published Unexamined Patent Application No. 61290/77).

An efficient process for producing L-isoleucine is always in demand from an industrial viewpoint.

SUMMARY OF THE INVENTION

According to the present invention, L-isoleucine can be produced in high yields at lower costs by culturing in a medium a microorganism belonging to the genus Escherichia and having resistance to S-(2-aminoethyl)-L-cysteine or D-serine and an ability to produce L-isoleucine, allowing L-isoleucine to accumulate in the culture, and recovering L-isoleucine therefrom.

DETAILED DESCRIPTION OF THE INVENTION

In the present invention, any microorganism can be used so long as it belongs to the genus Escherichia, has resistance to S-(2-aminoethyl)-L-cysteine or D-serine and has an ability to produce L-isoleucine.

The suitable microorganisms used in the present invention can be obtained by subjecting L-isoleucine producing microorganisms belonging to the genus Escherichia to conventional mutagenesis such as treatment with N-methyl-N'-nitro-N-nitrosoguanidine and X-ray irradiation, spreading the resulting microorganisms on a minimum agar plate medium containing S-(2-aminoethyl)-L-cysteine or D-serine, and picking up colonies which grow on the minimum agar plate medium.

Alternatively, the suitable microorganisms can be obtained by subjecting a mutant having resistance to S-(2-aminoethyl)-L-cysteine or D-serine derived from a wild strain to mutagenesis to enhance its L-isoleucine productivity.

Examples of the preferred microorganisms are *Escherichia coli* H-8670 and *Escherichia coli* H-8683.

According to the present invention, production of L-isoleucine can be carried out by culturing the above microorganisms in a conventional manner. As the medium, any synthetic or natural medium may be used so long as it appropriately contains carbon sources, nitrogen sources, inorganic compounds and trace amounts of other nutrients which the strain used requires.

As the carbon source, carbohydrates such as glucose, fructose, lactose, molasses, cellulose hydrolyzate, hydrolyzate of crude sugar and starch hydrolyzate; and organic acids such as pyruvic acid, acetic acid, fumaric acid, malic acid and lactic acid, can be used. Further, glycerol, alcohols such as ethanol, etc. can also be used provided that they can be assimilated by the strain used.

As the nitrogen source, ammonia; various inorganic salts such as ammonium chloride, ammonium sulfate, ammonium acetate and ammonium phosphate; ammonium salts of organic acids, amines and other nitrogen-containing compounds, peptone, meat extract, corn steep liquor, casein hydrolyzate, soybean cake hydrolyzate, various cultured cells and their digested product, etc. can be used.

As the inorganic compound, potassium dihydrogenphosphate, dipotassium hydrogenphosphate, magnesium phosphate, magnesium sulfate, sodium chloride, ferrous sulfate, manganese sulfate, copper sulfate, calcium carbonate, etc. can be used.

Culturing is carried out under aerobic conditions, e.g. by shaking culture and agitation submerged culture with aeration, at a temperature of 20° to 40° C., preferably 25° to 38° C. The pH of the medium is in the range of 5 to 9, and is preferably maintained at around neutrality. The pH is adjusted with calcium carbonate, inorganic or organic acids, alkaline solutions, ammonia, pH buffer agents, or the like.

Usually, after culturing for 2 to 7 days, L-isoleucine is accumulated in the culture.

After the completion of culturing, precipitates such as cells are removed from the culture by means of centrifugation, etc., and L-isoleucine can be recovered from the supernatant by using ion exchange treatment, concentration, salting-out, etc. in combination.

Certain embodiments of the invention are illustrated in the following examples.

EXAMPLE 1

Preparation of a Mutant Strain Having Resistance to S-(2-aminoethyl)-L-cysteine

*Escherichia coli* H-8664 derived from *Escherichia coli* H-8285 (FERM BP-3629) and having methionine-requirement, α-amino-β-hydroxyvaleric acid-resistance, rifampicin-resistance, thiaisoleucine-resistance, arginine hydroxamate-resistance and DL-ethionine-resistance was subjected to a conventional mutation treatment with N-methyl-N'-nitro-N-nitrosoguanidine (0.2 mg/ml, 33° C. 30 minutes), and then spread on a minimum agar plate medium (0.5% glucose, 0.1% ammonium chloride, 0.3% potassium dihydrogenphosphate, 0.6% disodium hydrogenphosphate, 0.01% magnesium sulfate, 20 mg/l calcium chloride, 2% agar, pH 7.2) containing 0.2 gl S-(2-aminoethyl)-L-cysteine, 3 g/l DL-methionine and 10 g/l L-threonine. After culturing at 33° C. for 2 to 5 days, large colonies which grew on the medium were picked up as the mutant strains having resistance to S-(2-aminoethyl)-L-cysteine and subjected to the L-isoleucine production test to select strains having L-isoleucine-producing ability greater than that of the parent strain. Among the thus selected strains was *Escherichia coli* H-8670.

The H-8670 strain thus obtained was deposited on Oct. 22, 1992 with the Fermentation Research Institute, Agency of Industrial Science and Technology, Japan under the Budapest Treaty with accession number FERM BP-4051.

The H-8670 strain was compared with the parent strain in degree of resistance to S-(2-aminoethyl)-L-cysteine in the following manner.

The mutant strain and the parent strain were cultured on a natural agar plate medium (1% trypton, 0.5% yeast extract, 1% sodium chloride, 2% agar, pH 7.2) for 24 hours. The cultured cells were suspended in sterilized water, and the cell suspension was spread to give a density of about $1\times10^3$ cells/$cm^2$ on the above-mentioned minimum agar plate medium containing S-(2-aminoethyl)-L-cysteine in the amounts shown in Table 1, 3 g/l DL-methionine and 10 g/l L-threonine. Culturing was carried out at 33° C. for 72 hours, and the degree of growth was observed. The degree of resistance to S-(2-aminoethyl)-L-cysteine was expressed in terms of degree of growth.

The results are shown in Table 1.

TABLE 1

| Strain | Amount of S-(2-aminoethyl)-L-cysteine (g/l) | | |
|---|---|---|---|
| | 0 | 0.2 | 0.8 |
| H-8664 | + | − | − |
| H-8670 | + | + | + |

+: sufficient growth
−: no growth

EXAMPLE 2

L-Isoleucine Production Test

*Escherichia coli* H-8670 obtained in Example 1 and the parent strain *Escherichia* coli H-8664 were inoculated into 20 ml of a seed medium (2% glucose, 1% peptone, 1% yeast extract, 0.25% sodium chloride, pH 7.0) in a 300-ml Erlenmeyer flask, and cultured with shaking at 30° C. for 16 hours. The resulting seed culture (2 ml) was inoculated into 100 ml of a fermentation medium (6% glucose, 0.2% corn steep liquor, 1.6% ammonium sulfate, 0.1% potassium dihydrogenphosphate, 100 mg/l DL-methionine, 4% magnesium phosphate, 1% calcium carbonate, pH 7.0) in a 2-l Erlenmeyer flask, and cultured with shaking at 30° C. for 72 hours.

After the completion of culturing, the amount of L-isoleucine accumulated was determined by high performance liquid chromatography. The results are shown in Table 2.

TABLE 2

| Strain | L-Isoleucine (g/l) |
|---|---|
| H-8664 | 9.0 |
| H-8670 | 12.2 |

One liter of the L-isoleucine-containing culture obtained by culturing the H-8670 strain was centrifuged (3000 rpm, 10 minutes) to remove the cells and other impurities therefrom. The obtained supernatant was passed through a column packed with a strongly acidic cation exchange resin, DIAION (type $H^+$; product of Mitsubishi Kasei Corporation, Japan), to adsorb L-isoleucine thereon. The column was washed with water, and subjected to elution with 0.5N aqueous ammonia to collect L-isoleucine fractions. The collected fractions were concentrated and ethanol was added to the concentrate. By storing the mixture under cooling, 10.3 g of L-isoleucine crystals having purity of 98% or higher was obtained.

EXAMPLE 3

Preparation of a Mmutant Strain Having Resistance to D-serine

*Escherichia coli* H-8670 (FERM BP-4051) obtained in Example 1 was subjected to a conventional mutation treatment with N-methyl-N'-nitro-N-nitrosoguanidine (0.2 mg/ml, 33° C., 30 minutes), and then spread on a minimum agar plate medium (0.5% glucose, 0.1% ammonium chloride, 0.3% potassium dihydrogenphosphate, 0.6% disodium hydrogenphosphate, 0.01% magnesium sulfate, 20 mg/l calcium chloride, 2% agar, pH 7.2) containing 20 g/l D-serine and 3 g/l DL-methionine. After culturing at 33° C. for 2 to 5 days, large colonies which grew on the medium were picked up as the mutant strains having resistance to D-serine and subjected to the L-isoleucine production test to select strains having L-isoleucine-producing ability greater than that of the parent strain. Among the thus selected strains was *Escherichia coli* H-8683.

The H-8683 strain thus obtained was deposited on Oct. 22, 1992 with the Fermentation Research Institute, Agency of Industrial Science and Technology, Japan under the Budapest Treaty with accession number FERM BP-4052.

The H-8683 strain was compared with the parent strain in degree of resistance to D-serine in the following manner.

The mutant strain and the parent strain were cultured on a natural agar plate medium (1% trypton, 0.5% yeast extract, 1% sodium chloride, 2% agar, pH 7.2) for 24 hours. The cultured cells were suspended in sterilized water, and the cell suspension was spread to give a density of about $1\times10^3$ cells/$cm^2$ on the above-mentioned minimum agar plate medium containing D-serine in the amounts shown in Table 3 and 3 g/l DL-methionine. Culturing was carried out at 33° C. for 72 hours, and the degree of growth was observed. The degree of resistance to D-serine was expressed in terms of degree of growth.

The results are shown in Table 3.

TABLE 3

| Strain | Amount of D-Serine (g/l) | | |
|---|---|---|---|
| | 0 | 3 | 20 |
| H-8670 | + | + | − |
| H-8683 | + | + | + |

+: sufficient growth
−: no growth

EXAMPLE 4

L-Isoleucine Production Test

*Escherichia coli* H-8683 obtained in Example 3 and the parent strain *Escherichia coli* H-8670 were inoculated into 20 ml of a seed medium (2% glucose, 1% peptone, 1% yeast extract, 0.25% sodium chloride, pH 7.0) in a 300-ml Erlenmeyer flask, and cultured with shaking at 30° C. for 16 hours. The resulting seed culture (2 ml) was inoculated into 100 ml of a fermentation medium (6% glucose, 0.2% corn steep liquor, 1.6% ammonium sulfate, 0.1% potassium dihydrogenphosphate, 100 mg/l DL-methionine, 4% magnesium phosphate, 1% calcium carbonate, pH 7.0) in a 2-l Erlenmeyer flask, and cultured with shaking at 30° C. for 72 hours.

After the completion of culturing, the amount of L-isoleucine accumulated was determined by high performance liquid chromatography. The results are shown in Table 4.

TABLE 4

| Strain | L-Isoleucine (g/l) |
|---|---|
| H-8670 | 12.2 |
| H-8683 | 14.1 |

One liter of the L-isoleucine-containing culture obtained by culturing the H-8683 strain was centrifuged (3000 rpm, 10 minutes) to remove the cells and other impurities therefrom. The obtained supernatant was passed through a column packed with a strongly acidic cation exchange resin, DIAION (type $H^+$; product of Mitsubishi Kasei Corporation, Japan), to adsorb L-isoleucine thereon. The column was washed with water, and subjected to elution with 0.5N aqueous ammonia to collect L-isoleucine fractions. The collected fractions were concentrated and ethanol was added to the concentrate. By storing the mixture under cooling, 11.9 g of L-isoleucine crystals having purity of 98% or higher was obtained.

What is claimed is:

1. A process for the production of L-isoleucine by fermentation, which comprises:

culturing in a nutrient medium a microorganism selected from the group consisting of *Escherichia coli* H-8670 (FERM BP-4051) and *Escherichia coli* H-8683 (FERM BP-4052) for a time and under conditions to produce said L-isoleucine;

and recovering L-isoleucine.

2. The process according to claim 1 wherein at least 12.2 g/l of L-isoleucine is produced.

3. The process according to claim 1 wherein said microorganism is *Escherichia coli* H-8683 (FERM BP-4052).

4. The process according to claim 3 wherein at least 14.1 g/l of L-isoleucine is produced.

* * * * *